(12) United States Patent
Zanella

(10) Patent No.: US 7,879,894 B2
(45) Date of Patent: Feb. 1, 2011

(54) USE OF ANTI-CYTOKINE AGENTS FOR TREATING CARPAL AND TARSAL TUNNEL SYNDROME

(75) Inventor: John M. Zanella, Cordova, TN (US)

(73) Assignee: Warsaw Orthopedic, Inc.

( * ) Notice: Subject to any disclaimer, the term of this patent is extended or adjusted under 35 U.S.C. 154(b) by 607 days.

(21) Appl. No.: 11/563,920

(22) Filed: Nov. 28, 2006

(65) Prior Publication Data

US 2008/0124383 A1 May 29, 2008

(51) Int. Cl.
*A61K 31/4168* (2006.01)
*A61F 2/00* (2006.01)

(52) U.S. Cl. .................. 514/392; 424/422; 424/423

(58) Field of Classification Search .................. None
See application file for complete search history.

(56) References Cited

U.S. PATENT DOCUMENTS

| | | | | |
|---|---|---|---|---|
| 4,673,637 | A * | 6/1987 | Hyman | 435/34 |
| 6,015,557 | A | 1/2000 | Tobinick et al. | |
| 6,177,077 | B1 | 1/2001 | Tobinick | |
| 6,193,991 | B1 * | 2/2001 | Shukla | 424/426 |
| 6,419,944 | B2 | 7/2002 | Tobinick | |
| 6,537,549 | B2 | 3/2003 | Tobinick | |
| 6,635,250 | B2 | 10/2003 | Olmarker et al. | |
| 6,649,589 | B1 | 11/2003 | Olmarker et al. | |
| 7,115,557 | B2 | 10/2006 | Olmarker | |
| 2003/0022813 | A1 * | 1/2003 | Chaplan et al. | 514/1 |

FOREIGN PATENT DOCUMENTS

WO  WO00/18409  4/2000

OTHER PUBLICATIONS

Robert R. Myers et al., "The Role of Neuroinflammation in Neuropathic Pain: Mechanisms and Therapeutic Targets," Drug Discovery Today, Elsevier Ltd., vol. 11 (No. 1/2), pp. 8-20 (2006).

P. Goupille et al., "Radiculopathy associated with disc herniation," Ann Rheum Dis, vol. 65, pp. 141-143 (2006).

R. G. Cooper et al., "TNF-alpha blockade for herniated intervertebral disc-induced sciatica: a way forward at last?," Rheumatology, vol. 43, pp. 119-121 (2004).

Maria Schaefers et al., "Increased Sensitivity of Injured and Adjacent Uninjured Rat Primary Sensory Neurons to Exogenous Tumor Necrosis Factor-alpha after Spinal Nerve Ligation," The Journal of Neurosciences, vol. 23 (No. 7), pp. 3028-3038 (2003).

Edward L. Tobinick, MD, "Targeted Etanercept for Discogenic Neck Pain: Uncontrolled, Open-Label Results in Two Adults," Clinical Therapeutics, vol. 25(No. 4) pp. 1211-1218, (2003).

Yuko Homma et al., "A comparison of chronic pain behavior following local application of tumor necrosis factor alpha to the normal and mechanically compressed lumbar ganglia in the rat," Pain, vol. 95 pp. 239-246 (2002).

Edward L. Tobinick et al., "Perispinal TNF-alpha inhibition for discogenic pain," Swiss Medical Weekly, vol. 133, pp. 170-177 (2003).

* cited by examiner

*Primary Examiner*—Marianne P Allen

(57) ABSTRACT

Methods for treating carpal tunnel syndrome and tarsal tunnel syndrome in a subject involve providing an effective amount of an anti-cytokine agent at or near inflammation in the carpal or tarsal tunnel. Anti-cytokine agents, such as, TNF-a inhibitors, NF-κB inhibitors, IL-1 inhibitors, IL-6 inhibitors, IL-8 inhibitors, IL-12 inhibitors, IL-15 inhibitors, IL-10, Interferon-gamma (IFN-?) act to prevent further inflammation initiated by cytokine factors. One embodiment includes, adding with the anti-cytokine agent one or more of an antibiotic or analgesic. Delivery of the anti-cytokine agent may be provided to the inflamed tissue of the carpal or tarsal tunnel by injection, implantation, or a transdermal patch. These agents, individually or in combination, directly address the underlying inflammation that causes the discomfort, pain, and restricted movement associated with carpal and tarsal tunnel syndrome.

16 Claims, No Drawings

USE OF ANTI-CYTOKINE AGENTS FOR TREATING CARPAL AND TARSAL TUNNEL SYNDROME

FIELD OF THE INVENTION

The present invention relates to methods of treating carpal and tarsal tunnel syndrome in a subject by eliminating or reducing inflammation by providing an effective amount of an anti-cytokine agent at or adjacent to the site of painful inflammation of the carpal tunnel or tarsal tunnel.

BACKGROUND OF THE INVENTION

Carpal and tarsal tunnel syndromes are painful, progressive conditions caused by compression of a key nerve in the wrist or ankle, respectively. Carpal tunnel syndrome occurs when the median nerve, which runs from the forearm into the hand, becomes pressed or squeezed at the wrist. Tarsal tunnel syndrome occurs when the posterior tibial nerve, which runs from the leg to the ankle, where it divides into the medial and lateral plantar nerves, becomes compressed. Non-steroidal anti-inflammatory drugs, such as aspirin, ibuprofen, and other nonprescription pain relievers, may ease pain. Cool (ice) packs and prednisone (taken orally) or lidocaine (injected directly into the wrist or ankle) can relieve swelling and pressure on the nerve and provide immediate but temporary relief. A doctor may treat the condition with a corticosteroid to decrease inflammation, thus relieving pressure on the nerve. In persistent or severe cases, surgery may be necessary to decompress the tunnel.

Inflammation can be an acute response to trauma or a chronic response to the presence of inflammatory agents. When tissues are damaged, TNF-a attaches to cells to cause them to release other cytokines that cause inflammation. The purpose of the inflammatory cascade is to promote healing of the damaged tissue, but once the tissue is healed the inflammatory process does not necessarily end. Left unchecked, this can lead to degradation of surrounding tissues and associated chronic pain. Thus, pain can become a disease state in itself. That is, when this pathway is activated, inflammation and pain ensue. Often a vicious and seemingly endless cycle of insult, inflammation, and pain sets in. There are numerous examples of conditions in which this cycle is present including, but not limited to, the tendons and soft tissue surrounding and passing through the carpal and tarsal tunnels.

The carpal tunnel is located in the wrist and is surrounded by bone and a fibrous band of tissue, the flexor retinaculum. The median nerve passes through the carpal tunnel along with several flexor tendons. Pain associated with carpal tunnel syndrome results from compression of the median nerve, which may be caused by, inter alia, inflammation of the flexor tendons or swelling of the soft tissue in or around the tunnel. In addition to discomfort, inhibited sensation, and pain, persons suffering from carpal tunnel syndrome frequently have reduced flexibility and range of motion in the wrist.

The tarsal tunnel is located at the medial side of the ankle and is surrounded by bone and the flexor retinaculum. The posterior tibial nerve, which divides into the medial and lateral plantar nerves, passes through the tarsal tunnel along with several flexor tendons, the posterior tibialis artery, and two accompanying veins. The tibial nerve most commonly divides into the medial and lateral plantar nerves while in the tarsal tunnel; however, the tibial nerve divides proximal to the entrance of the tunnel in about five percent of individuals. For purposes of this specification, discussion of the tibial nerve includes the medial and lateral plantar nerves in cases where division occurs proximal to or in the tarsal tunnel. Similar to carpal tunnel syndrome, the pain associated with tarsal tunnel syndrome may result from, inter alia, inflammation of the flexor tendons or surrounding soft tissue. In addition to the tarsal tunnel, compression in the calcaneal tunnel, medial plantar tunnel, and lateral plantar tunnel also contribute to the symptoms of tarsal tunnel syndrome. For the purposes of this specification, any discussion of the tarsal tunnel or the region at or adjacent to the tarsal tunnel includes the calcaneal, medial plantar, and lateral plantar tunnels.

As mentioned above, inflammation of tendons in the carpal and tarsal tunnels are one cause of the syndromes. A normal tendon connects muscle to bone and allows transmission of forces generated by the muscle to the bone, causing joint movement. Tendons are hierarchical structures comprised of longitudinally oriented collagen fibers, which are clustered within a microfibril, which in turn are clustered to form subfibrils, fibrils, fascicles, and finally the tendon. Each level of microanatomy has a similar overall structure of fibers within an extracellular proteoglycan matrix with a paucity of cells dominated by fibroblasts. Cells are present between collagen fibers, and, at the fascicle level of microanatomy, a loose connective tissue invests itself between fascicles and is termed the endotenon, which permits longitudinal movement of fascicles and allows room for blood vessels, lymphatics, and nerves. The epitenon, a loose connective-tissue sheath containing the vascular, lymphatic and nerve supply to the tendon covers the whole tendon and extends deep within the endotenon. The epitenon, is surrounded by paratenon and an inner lining of synovial cells. During an injury to the tendon, damaged cells within the tendon don't have time to recuperate. The cells are unable to repair themselves, causing a chain reaction and leading to tendonitis. When this happens in the tendon, inflammation, or even a rupture of the tendon, may occur. This is common in sport or work activities that require frequent and repeated use of the arm, especially when the arm motions are performed overhead. Degeneration in a tendon causes a loss of the normal arrangement of the collagen fibers that join together to form the tendon. Some of the individual strands of the tendon become weakened due to the degeneration, other fibers break, and the tendon loses strength. See G. Riley, *The pathogenesis of tendinopathy. A molecular perspective, Rheumatology,* 2004; 43:131-142 (July 2003).

Inflammation is believed to affect disease progression and pain in carpal and tarsal tunnel syndrome. Inflammation can stimulate angiogenesis, and angiogenesis was believed to facilitate inflammation. Inflammation sensitizes nerves, leading to increased pain. Inhibition of inflammation and angiogenesis may provide effective therapeutics for the treatment of osteoarthritis by improving symptoms and retarding joint damage. See C. S. Bonnet et al., *Rheumatology, Oxford Journals,* 2005; 44:7-16.

Inflammation is recognized to be a key event in the development of normal cartilage and bone. By promoting the delivery of nutrients, oxygen, and cells, blood vessels help maintain the structural and functional integrity of joints and soft tissue and may facilitate tissue repair and healing. The identification of pro-angiogenic mediators, such as vascular endothelial growth factor, has led to the development of anti-angiogenic therapies for the treatment of neoplastic diseases. While not being bound by any theory, the important role of angiogenesis in the pathogenesis of joint disorders, such as rheumatodial arthritis, led to the suggestion that anti-angiogenic therapy may be a useful adjunct to existing approaches in the treatment of rheumatodial arthritis. See Ballara S. C. et al., *J. Exp. Pathol.,* 1999, October; 80(5):235-50.

It is therefore desirable to provide improved methods of treating carpal and tarsal tunnel syndrome that avoid the drawbacks of the prior art. Specifically, rather than using corticosteroids, it is possible to treat the inflammatory response with anti-cytokine agents such as TNF-a inhibitors, IL-1 inhibitors, IL-6 inhibitors, IL-8 inhibitors, IL-12 inhibitors, IL-10, autologous blood-derived products (i.e., Orthokine), NF-?B inhibitors, Interferon-gamma (IFN-?), etc.

SUMMARY OF INVENTION

The present invention fills the foregoing need by providing methods for treating carpal and tarsal tunnel syndrome by providing an effective amount of an anti-cytokine agent at or near the carpal and tarsal tunnels. In particular, the anti-cytokine agent inhibits the rapid pro-inflammatory response in the tendons and tissue in or surrounding the tunnel. While not being bound by any theory, applicants believe that prevention of pro-inflammatory cytokines will reduce and/or alleviate inflammation of the tendons and soft tissue in or around the carpal and tarsal tunnels, thereby reducing or eliminating compression of the median nerve and posterior tibial nerve, respectively.

One aspect provides a method of treating carpal or tarsal tunnel syndrome in a subject comprising providing an effective amount of an anti-cytokine agent at or near a site of inflammation in or near the carpal or tarsal tunnel, wherein said anti-cytokine agent is administered through a controlled administration system, transdermal patch, or carrier.

The method may additionally comprises the anti-cytokine agent being selected from the group consisting of TNF-a inhibitors, IL-1 inhibitors, IL-6 inhibitors, IL-8 inhibitors, IL-12 inhibitors, IL-15 inhibitors, IL-10, NF-?B inhibitors, and IFN-?. Furthermore, the carrier may be selected from the group consisting of capsules, microspheres, particles, gels, coatings, matrices, wafers, pills, and other pharmaceutical delivery compositions.

In another aspect of the invention, the controlled administration system may comprise a sustained release formulation, which may further comprise a carrier or biodegradable polymer. The controlled administration system of the method may also comprise a depot, infusion pump, osmotic pump, implantable mini pump, peristaltic pump, or catheter. In this sense, a depot refers to capsules, microspheres, particles, gels, coatings, matrices, wafers, pills, other pharmaceutical delivery compositions, and similar or equivalent compositions.

A preferred embodiment includes administering the anti-cytokine agent by means of a biodegradable depot introduced at or adjacent to the site of painful inflammation of a tendon, soft tissue, or other inflammation in or near the carpal or tarsal tunnel.

The anti-cytokines of the present methods prevent, inhibit, or reduce inflammation of a tendon or soft tissue in or near the carpal or tarsal tunnel. In one aspect of the methods, one or more active ingredients are added to the formulation with an anti-cytokine agent and administered at or near the inflammation. The active ingredients are preferably antibiotics, analgesics, or any combination thereof. In one embodiment, such active ingredients may be incorporated into a carrier, which may also contain the anti-cytokine agent. Additionally, the carrier may be biodegradable and may comprise any generally known pharmacological excipient.

It is intended that the anti-cytokine agents of the present invention prevent or inhibit pro-inflammatory responses in the tendons and soft tissue in or near the carpal and tarsal tunnels. Additionally, the anti-cytokine agent is adapted to disrupt inflammatory elements at or adjacent to the site of painful inflammation of a tendon, of tissue, or other inflammation in or near the carpal or tarsal tunnel. The anti-cytokine agent may include, for example, a pro-inflammatory receptor antagonist such as an anti-TNF-a agent, which will effectively compete for the TNF-a receptor and inhibit a pro-inflammatory response.

Another aspect of the present invention provides a method for treating carpal or tarsal tunnel syndrome in a subject comprising providing an effective amount of an anti-cytokine agent and optionally an active ingredient to inflamed tissue in the carpal or tarsal tunnel, respectively, wherein the anti-cytokine agent is administered through an injection, pump, transdermal patch, carrier, or depot.

DETAILED DESCRIPTION OF THE INVENTION

The present invention relates to methods of treating carpal and tarsal tunnel syndrome in a subject comprising providing an effective amount of an anti-cytokine agent at or near a site of inflammation in or near the carpal or tarsal tunnel, wherein said anti-cytokine agent is administered through a controlled administration system, transdermal patch, or carrier.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

Definitions

To aid in the understanding of the invention, the following non-limiting definitions are provided:

The term "carpal tunnel syndrome" is defined as a progressive condition caused by compression of the median nerve due to local inflammation.

The term "tarsal tunnel syndrome" is defined as a progressive condition caused by compression of the posterior tibial nerve and/or the medial and lateral plantar nerves due to local inflammation.

The term "musculo-tendinous structure" is defined as the insertion point at which a tendon attaches to bone and muscle, such as, for example, the Achilles tendon that connects the heel to the muscles of the lower leg.

The term "tendinopathy" describes a type of tendon injury that occurs when the tendon becomes painful or torn. This may be a result of tendon inflammation and/or microtears in the connective tissue in or around the tendon.

The term "anti-cytokine agent" shall mean any molecule, cell, or physical stimulus which decreases, blocks, inhibits, abrogates or interferes with the pro-inflammatory cascade of cytokine proteins leading to an inflammatory response. For example, a suitable "tumor necrosis factor alpha antagonist" or "TNF-a" antagonist can bind TNF, and includes anti-TNF antibodies and/or receptor molecules which bind specifically to TNF. A suitable TNF antagonist can also prevent or inhibit TNF synthesis and/or TNF release and includes compounds such as thalidomide, tenidap, and phosphodiesterase inhibitors, such as, but not limited to, pentoxifylline and rolipram.

As used herein, anti-cytokine agents include substances that are direct and local-acting modulators of the pro-inflammatory effect of TNF-a, such as but not limited to, soluble tumor necrosis factor a receptors, any pegylated soluble tumor necrosis factor a receptor, monoclonal or polyclonal antibodies or antibody fragments or combinations thereof.

Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1?3-β-D-glucans, Lenercept, PEG-sTNFRII Fc Mutein, D2E7, Afelimomab, and combinations thereof. They can decrease pain through their actions as inhibitors or agonists of the release of pro-inflammatory molecules. For example, these substances can act by inhibiting or antagonizing expression or binding of cytokines or other molecules that act in the early inflammatory cascade, often resulting in the downstream release of prostaglandins and leukotrienes. These substances can also act, for example, by blocking or antagonizing the binding of excitatory molecules to nociceptive receptors in the nervous system or neuromuscular system, as these receptors often trigger an inflammatory response to inflammation or injury of the nerve or surrounding tissue through a nitric oxide-mediated mechanism. These biological response modifiers include, for example, inhibitors of the action of tumor necrosis factor alpha (TNF-a). Studies have demonstrated that in chronic arthritic diseases, for example, cartilage degradation continues even when the inflammation has been suppressed. Anti-cytokine agents such as anti-TNF agents may be particularly effective for treatment of carpal and tarsal tunnel syndrome, for example, because they may not only decrease the inflammation that provides the source of pain and restriction of movement but may also slow the progression of tendon and or bursa destruction that can accompany the inflammatory response. Hence, local targeted delivery of the anti-cytokine agents in accordance with the invention may reduce tendon and bursa necrosis and damage.

In one example of an alternative approach, the anti-cytokine agent is a TNF binding protein. One suitable such anti-cytokine agent is currently referred to as Onercept. Formulae including Onercept, Onercept-like agents, and derivatives are all considered acceptable. Still other suitable anti-cytokine agents include dominant-negative TNF variants. A suitable dominant-negative TNF variant includes but is not limited to DN-TNF and including those described by Steed et al. (2003), "Inactivation of TNF signaling by rationally designed dominant-negative TNF variants," *Science,* 301(5641):1895-1898. Still more embodiments include the use of a recombinant adeno-associated viral (rAAV) vector technology platform to deliver the oligonucleotides encoding inhibitors, enhancers, potentiators, neutralizers, or other modifiers. For example, in one embodiment a rAAV vector technology platform delivers the DNA sequence of a potent inhibitor of tumor necrosis factor (TNF-alpha). One suitable inhibitor is TNFR:Fc. Other anti-cytokine agents include antibodies, including but not limited to naturally occurring or synthetic, double-chain, single-chain, or fragments thereof. For example, suitable anti-cytokine agents include molecules based on single-chain antibodies, commonly known under the mark Nanobodies™ (Ablynx, Ghent Belgium), which are defined as the smallest functional fragment of a naturally occurring single-domain antibody.

It is understood that TNF is affected by upstream events which modulate its production and, in turn, affects downstream events. Alternative approaches to treating carpal and tarsal tunnel syndrome exploit this known fact, and antagonists are designed to specifically target TNF as well as molecules upstream or downstream or a combination thereof. Such approaches include but are not limited to modulating TNF directly, modulating kinases, inhibiting cell-signaling, manipulating second messenger systems, modulating kinase activation signals, modulating a cluster designator on an inflammatory cell, modulating other receptors on inflammatory cells, blocking transcription or translation of TNF or other targets in pathway, modulating TNF-a post-translational effects, employing gene silencing, or modulating interleukins, for example IL-1, IL-6 and IL-8.

Interleukin-1 is a pro-inflammatory cytokine similar in action to TNF-a. For example, certain inhibitors of this protein are similar to those developed to inhibit TNF-a. One such example is Kineret® (anakinra), which is a recombinant, non-glycosylated form of the human interleukin-1 receptor antagonist (IL-1Ra). Another suitable anti-cytokine agent is AMG 108, which is a monoclonal antibody that blocks the action of IL-1.

Still other anti-cytokine agents include but are not intended to be limited to NF Kappa B inhibitors, for example glucocorticoids such as flucinolonone; nonsteroidal anti-inflammatory drugs (NSAIDs) such as sulindac and tepoxalin; antioxidants such as dithiocarbamate; and other compounds such as sulfasalazine [2-hydroxy-5-[-4-[C2-pyridinylamino)sulfonyl]azo]benzoic acid], clonidine, and autologous blood-derived products such as Orthokine.

As used herein, "modulating" ranges from initiating to shutting down, and within that range is included enhancing significantly or slightly to inhibiting significantly or slightly. The term "inhibiting" includes a down-regulation which may reduce or eliminate the targeted function, such as the production of a protein or the translation of an oligonucleotide sequence. For example, a given patient's condition may require only inhibition of a single molecule, such as TNF, or modulating more than one molecule in a cascade of upstream and/or downstream events in the pathway.

Anti-cytokine agents which inhibit TNF-a-post translational effects are useful in the invention. For example, the initiation of a TNF-a signaling cascade results in the enhanced production of numerous factors that subsequently act in a paracrine and autocrine fashion to elicit further production of TNF-a as well as other pro-inflammatory agents (IL-1, IL-6, IL-8, HMG-B1). Extracellular TNF-a modifying anti-cytokine agents that act on the signals downstream of TNF-a are useful in treating systemic inflammatory diseases. Some of these anti-cytokine agents are designed to block other effector molecules while others block the cellular interaction needed to further induce their production, for example, integrins and cell adhesion molecules.

Suitable anti-cytokine agents include: integrin antagonists, alpha-4 beta-7 integrin agonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibody (daclizumab, basilicimab), ABX (anti IL-8 antibody), recombinant human IL-10, and HuMax IL-15 (anti-IL 15 antibody).

As indicated earlier, other suitable anti-cytokine agents include IL-1 inhibitors, such as Kineret® (anakinra) and AMG 108.

The term "pro-inflammatory" shall mean an endotoxin or stimuli that initiates monocytes and macrophages to secrete cytokines which lead to an inflammatory response, such as, for example, tumor necrosis factor alpha (TNF-a) and tumor necrosis factor beta (TNF-β).

The term "active ingredient" shall mean a biologically active ingredient that achieves a medically useful end, and in certain embodiments may specifically include antibiotics, analgesics, or any combination thereof.

The term "subject" shall mean any animal belonging to phylum Chordata, including, without limitation, humans.

The term "treating" or "treatment" of a disease refers to executing a protocol, which may include administering one or more drugs to a subject (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the subject.

Carriers

The anti-cytokine agent may be included into a carrier which is administered to a site of painful inflammation of the tendon or soft tissue or adjacent to such a site. Suitable non-limiting examples of carriers include a gel, such as, for example, a PEG gel, SABE gel, hydrogel, etc. The methods of incorporating the anti-cytokine agent into the carrier are known to a person of ordinary skill in the art and depend on the nature of the anti-cytokine agent and the nature of the carrier selected by a person practicing the current invention. Ionic binding, gel encapsulation or physical trapping inside the carrier, iontophoresis and soaking the carrier in a solution of the anti-cytokine agent are suitable examples of such methods. Alternatively, the carrier may be little more than a diluent for the anti-cytokine agent.

Active Ingredients

In different embodiments of the invention, an active ingredient may also be added to the carrier. The active ingredient may include an antibiotic, an analgesic, and any combination thereof, in addition to one or more anti-cytokine agents.

Suitable analgesics include morphine and naloxone, local anaesthetics (such as, for example, lidocaine), glutamate receptor antagonists, adrenoreceptor agonists, adenosine, canabinoids, cholinergic and GABA receptors agonists, and different neuropeptides. A detailed discussion of different analgesics is provided in Sawynok et al., (2003) *Pharmacological Reviews*, 55:1-20, the content of which is incorporated herein by reference.

Suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol and any combination thereof.

Sustained-Release Formulations

In another embodiment of the present invention, the anti-cytokine agent and, optionally, any other active ingredients may be presented in a sustained-release formulation. Carriers suitable for sustained-release formulations include, but are not limited to, capsules, microspheres, particles, gels, coatings, matrices, wafers, pills or other pharmaceutical delivery compositions. Examples of such sustained-release formulations have been described previously, for example, in U.S. Pat. Nos. 6,953,593, 6,946,146, 6,656,508, 6,541,033, 6,451,346, the contents of which are incorporated herein by reference. Many methods for preparation of a sustained-release formulation are known in the art, and are disclosed in *Remington's Pharmaceutical Sciences* (18th ed.; Mack Publishing Company, Eaton, Pa., 1990), incorporated herein by reference.

Generally, the anti-cytokine agent can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate (Sidman et al., *Biopolymers* 22:547-556 (1983)), polylactides (U.S. Pat. No. 3,773,919 and EP 58,481), polylactate polyglycolate (PLGA) such as polylactide-co-glycolide (see, for example, U.S. Pat. Nos. 4,767,628 and 5,654,008), hydrogels (see, for example, Langer et al. (1981) *J. Biomed. Mater. Res.* 15:167-277; Langer, *Chem. Tech.* 12:98-105 (1982)), non-degradable ethylene-vinyl acetate (e.g. ethylene vinyl acetate disks and poly(ethylene-co-vinyl acetate)), degradable lactic acid-glycolic acid copolyers such as the Lupron Depot™, poly-D-(−)-3-hydroxybutyric acid (EP 133,988), hyaluronic acid gels (see, for example, U.S. Pat. No. 4,636,524), alginic acid suspensions, polyorthoesters (POE), and the like.

Suitable microcapsules capable of encapsulating the anti-cytokine agent may also include hydroxymethylcellulose or gelatin-microcapsules and polymethyl methacrylate microcapsules prepared by coacervation techniques or by interfacial polymerization. See PCT publication WO 99/24061 entitled "Method for Producing Sustained-release Formulations," wherein a protein is encapsulated in PLGA microspheres, incorporated herein by reference. In addition, microemulsions or colloidal drug delivery systems such as liposomes and albumin microspheres, may also be used. See *Remington's Pharmaceutical Sciences* (18th ed.; Mack Publishing Company Co., Eaton, Pa., 1990). Other preferred sustained-release compositions employ a bioadhesive to retain the anti-cytokine agent at the site of administration.

The sustained-release formulation may comprise a biodegradable polymer into which the anti-cytokine agent is disposed, which may provide for non-immediate release. Non-limiting examples of biodegradable polymers suitable for the sustained-release formulations include poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described, for example, in the U.S. Pat. No. 6,991,654 and U.S. Pat. Appl. No. 20050187631, each of which is incorporated herein by reference in its entirety.

A person of ordinary skill will appreciate that different combinations of the sustained-release formulations are also suitable for this invention. For example, the practitioner may formulate at least one anti-cytokine agent as a combination of a gel and microspheres loaded with the at least one anti-cytokine, wherein the combination of gel and microspheres are placed in the target site.

In the practice of the invention, the administration may be localized and sustained. For example, depending on the carrier, the sustained-release formulations, and the total amount of the anti-cytokine, release of the active material (including the optional active ingredient) over a desired time period ranging between about one day to about six months is possible.

In yet other embodiments, further excipients are employed. The amount of excipient that is useful in the composition of this invention is an amount that serves to uniformly distribute the anti-cytokine, and other active ingredients, throughout the composition so that it can be uniformly dispersed when it is to be delivered to a subject in need thereof. It may serve to dilute the anti-cytokine to a concentration at which the anti-cytokine can provide the desired beneficial palliative or curative results while at the same time minimizing any adverse side effects that might occur from too high a concentration. It may also have a preservative effect. Thus, for the anti-cytokine that has a high physiological activity, more of the excipient will be employed. On the other hand, for the anti-cytokine compound that exhibits a lower physiological activity, a lesser quantity of the excipient will be employed. In general, the amount of excipient in the composition will be between about 50% weight (w) and 99.9% w. of the total composition. Of course, if the anti-cytokine compound exhibits a particularly low physiological activity, the amount of excipient could be as little as 1% w. On the other hand, for the anti-cytokine that has a particularly high physiological activity, the amount of excipient may be between about 98.0% and about 99.9% w.

Accordingly, the methods of creating the sustained-release formulations comprising the at least one anti-cytokine agents and/or the active ingredient are within the expertise of the person having ordinary skill in the art.

The anti-cytokine agent may be administered locally. In one embodiment, the anti-cytokine agent has a targeted release rate and is injected into or near the musculo-tendinous structure or soft tissue at or near the site of painful inflammation. In another embodiment, a controlled administration system releases the anti-cytokine agent. The controlled administration system may be, for example, a depot, an infusion pump, an osmotic pump, implantable mini-pumps, a peristaltic pump, or other pharmaceutical pumps. The controlled administration system may be implanted adjacent to the site of inflammation causing pressure on the medial nerve or posterior tibial nerve. In yet another embodiment, the controlled administration system comprises a system administered locally by insertion of a catheter at or near a target site, the catheter having a proximal end and a distal end, the distal end having an opening to deliver a pharmaceutical in situ, the proximal end being fluidly connected to a pharmaceutical delivery pump. For example, the distal end of the catheter delivers the anti-cytokine agent within 10 cm of the painful inflammation, and more particularly, within 5 cm of the inflammation.

A depot includes, but is not limited to, capsules, microspheres, particles, gels, coatings, matrices, wafers, pills or other pharmaceutical delivery compositions for containing one or more active ingredients, for example an anti-cytokine in combination with one or more other active ingredients. A depot may comprise a biopolymer, and may be biodegradable. The biopolymer may provide for non-immediate release of the one or more active ingredients and anti-cytokine. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, and combinations thereof.

The anti-cytokine agent may be injected into the musculo-tendinous structure or the soft tissue in or surrounding the carpal or tarsal tunnel. This embodiment may be especially preferable. Additional examples of administering a pharmaceutical agent that may be usefully adapted to the instant invention can be found at Trieu et. al., U.S. Pat. Appl. No. 2004005414, U.S. Pat. Appl. No. 20040228901, U.S. Pat. Appl. No. 200540119754, and U.S. Pat. Appl. No. 20050197707. Alternatively, a transdermal patch suitably loaded with the anti-cytokine agent may be employed to locally administer the anti-cytokine agent to a target site. The patch may be applied, for example, to the region of skin immediately above and around the site of painful inflammation.

A person skilled in the art will appreciate that various modifications of these embodiments are possible. Among these modifications are different sustained-release formulations of the anti-cytokine agent and active ingredient.

Specific embodiments according to the methods of the present invention will now be described in the following non-limiting examples. Although the invention herein has been described with reference to particular embodiments, it is to be understood that these embodiments are merely illustrative of the principles and applications of the present invention.

EXAMPLE

Example 1

An anti-cytokine agent may be mixed with a biocompatible medium such as water, saline, or ethylene glycol and injected directly to the area around the musculo-tendinous structure, carpal tunnel, or tarsal tunnel using a syringe and a hypodermic needle. A single injection is effective for reducing the inflammation, although additional injections may be necessary to achieve appropriate levels of treatment.

Example 2

An anti-cytokine agent with an antibiotic and/or an analgesic may be mixed with a biocompatible medium such as water, saline, or ethylene glycol and injected directly at or near the carpal or tarsal tunnel using a syringe and a hypodermic needle. A single injection is effective for reducing the pain, although additional injections may be necessary to achieve appropriate levels of treatment.

Example 3

A biodegradable depot loaded with the anti-cytokine agent is placed into, or immediately adjacent to, a musculo-tendinous structure or the carpal or tarsal tunnel using any suitable method known in the art. The biodegradable depot may be manufactured using any of the methods indicated above, such as microencapsulation, biodegradable polymers, etc., and releases the anti-cytokine agent into the target site in a controlled manner. Single application of the biodegradable implant is desirable; however, additional implants may be necessary to achieve the appropriate levels of treatment.

Example 4

A transdermal patch imbued with the anti-cytokine agent is applied to the skin of the patient over the carpal or tarsal tunnel. The anti-cytokine agent leaches from the patch and diffuses through the patient's skin into the inflamed tissue.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

I claim:

1. A method of treating carpal or tarsal tunnel syndrome in a subject suffering from carpal or tarsal tunnel syndrome comprising implanting a formulation comprising an effective amount of clonidine and an antibiotic at or near a site of inflammation in or near the carpal or tarsal tunnel, wherein said formulation is administered through a controlled administration system, comprising a biodegradable polymer depot containing the formulation.

2. The method of claim 1, wherein the biodegradable polymer depot is selected from the group consisting of capsules, microspheres, particles, gels, coatings, matrices, and wafers.

3. The method of claim 1, wherein the formulation is encapsulated in microcapsules that comprise hydroxymethylcellulose, gelatin, or polymethyl methacrylate.

4. The method of claim 1, wherein the biodegradable polymer depot further comprises an excipient.

5. The method of claim 1, wherein the antibiotic is a nitroimidazole antibiotic.

6. The method of claim 1, wherein the antibiotic is tetracycline.

7. The method of claim 1, wherein the antibiotic is penicillin.

8. The method of claim 1, wherein the antibiotic is a cephalosporin.

9. The method of claim 1, wherein the antibiotic is a carbopenem.

10. The method of claim 1, wherein the antibiotic is an aminoglycoside.

11. The method of claim 1, wherein the antibiotic is a macrolide antibiotic.

12. The method of claim 1, wherein the antibiotic is a lincosamide antibiotic.

13. The method of claim 1, wherein the antibiotic is a 4-quinolone antibiotic.

14. The method of claim 1, wherein the antibiotic is rifamycin.

15. The method of claim 1, wherein the antibiotic is nitrofurantoin.

16. A method for treating carpal or tarsal tunnel syndrome in a subject suffering from carpal or tarsal tunnel syndrome comprising implanting a formulation comprising an effective amount of clonidine and an antibiotic locally to inflamed tissue in the carpal or tarsal tunnel, wherein the formulation is administered in a biodegradable polymer depot that releases the formulation over a period of one day to six months.

* * * * *

UNITED STATES PATENT AND TRADEMARK OFFICE
CERTIFICATE OF CORRECTION

| | | |
|---|---|---|
| PATENT NO. | : 7,879,894 B2 | Page 1 of 1 |
| APPLICATION NO. | : 11/563920 | |
| DATED | : February 1, 2011 | |
| INVENTOR(S) | : Zanella | |

It is certified that error appears in the above-identified patent and that said Letters Patent is hereby corrected as shown below:

In Column 2, Line 67, delete "al., J." and insert -- al., Int. J --, therefor.

Signed and Sealed this
Fifth Day of April, 2011

David J. Kappos
*Director of the United States Patent and Trademark Office*